(12) United States Patent
Bolin

(10) Patent No.: US 8,646,336 B2
(45) Date of Patent: Feb. 11, 2014

(54) METHOD FOR TESTING LIFT EQUIPMENT

(76) Inventor: Andreas Bolin, Gammelstad (SE)

( * ) Notice: Subject to any disclaimer, the term of this patent is extended or adjusted under 35 U.S.C. 154(b) by 307 days.

(21) Appl. No.: 13/253,137

(22) Filed: Oct. 5, 2011

(65) Prior Publication Data

US 2012/0085177 A1  Apr. 12, 2012

Related U.S. Application Data

(60) Provisional application No. 61/390,223, filed on Oct. 6, 2010.

(51) Int. Cl.
*G01N 3/00* (2006.01)
(52) U.S. Cl.
USPC ............................................ 73/788; 73/432.1
(58) Field of Classification Search
USPC ................................ 73/760, 788, 865.9, 432.1
See application file for complete search history.

(56) References Cited

U.S. PATENT DOCUMENTS

| | | | | |
|---|---|---|---|---|
| 4,351,431 A | * | 9/1982 | Fenton et al. | 198/823 |
| 4,502,327 A | * | 3/1985 | Scrivener et al. | 73/146 |
| 4,569,416 A | * | 2/1986 | Stokoe | 182/2.9 |
| 5,152,733 A | * | 10/1992 | Farenholtz et al. | 482/135 |
| 7,378,836 B2 | * | 5/2008 | Teoh et al. | 324/750.05 |
| 7,600,411 B2 | * | 10/2009 | Bailey | 73/9 |
| 2006/0075558 A1 | * | 4/2006 | Lambarth et al. | 5/611 |
| 2010/0275695 A1 | * | 11/2010 | Cotrell et al. | 73/663 |

\* cited by examiner

*Primary Examiner* — Max Noori
(74) *Attorney, Agent, or Firm* — Fasth Law Offices; Rolf Fasth

(57) ABSTRACT

The method is for testing load equipment. A trolley is provided that has a housing with an upwardly sloping front segment and an upwardly sloping rear segment. Upwardly directed weights are stacked side-by-side on the front and rear segments so that the weights lean towards each other. The trolley is stopped by engaging the brake support against the ground so that the front segment is substantially parallel to the ground. Weights are added or removed from the trolley by downwardly inserting or upwardly pulling, respectively, the weights without removing any of the wheels. The trolley is connected to lifting equipment. The lifting equipment lifts the trolley from the ground.

6 Claims, 3 Drawing Sheets

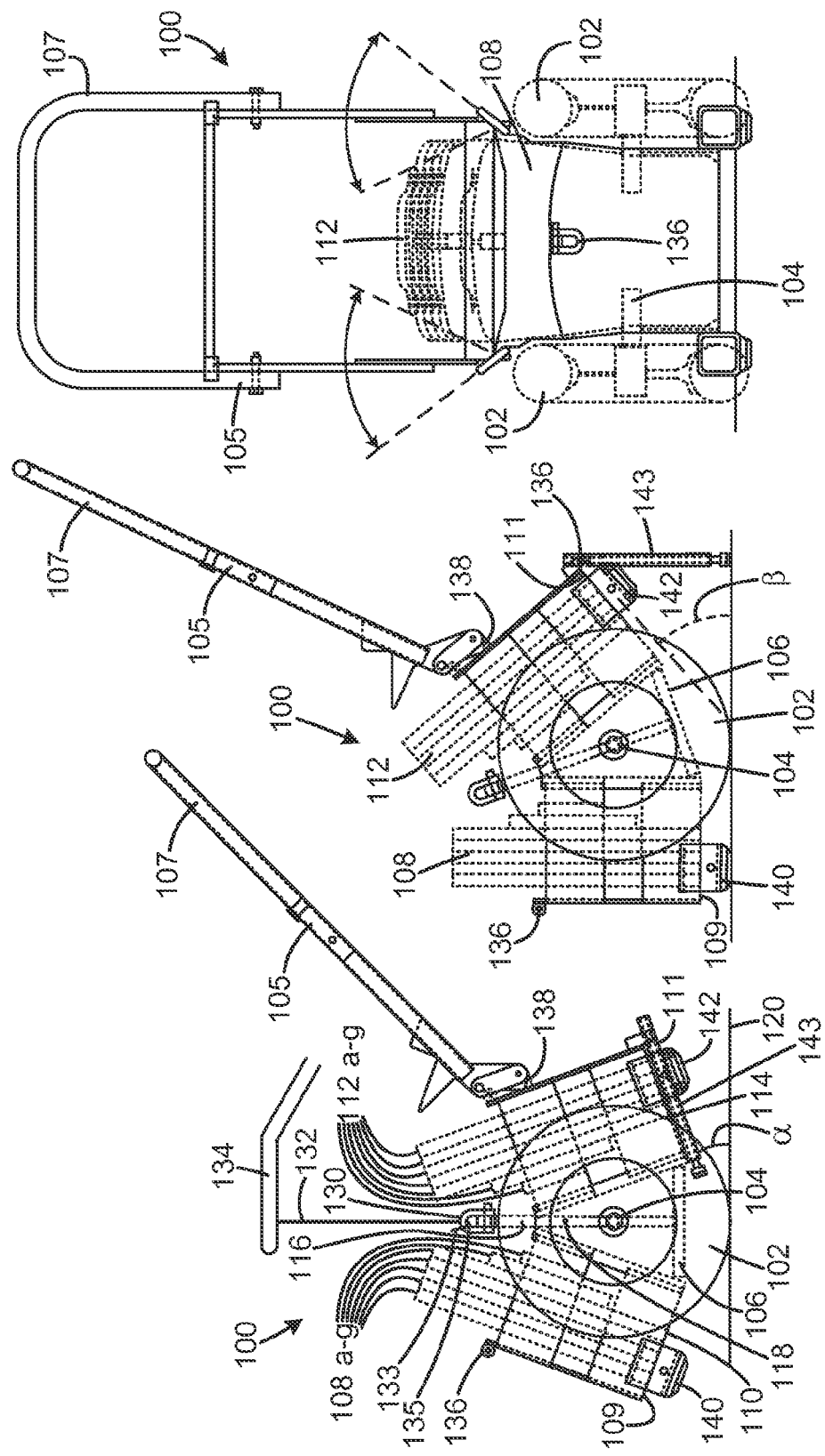

METHOD FOR TESTING LIFT EQUIPMENT

PRIOR APPLICATION

This is a US utility patent application that claims priority from U.S. provisional patent application Ser. No. 61/390,223, filed 6 Oct., 2010.

TECHNICAL FIELD

The invention relates to a method for testing lift equipment by using a trolley.

BACKGROUND OF INVENTION

Many different types of equipment for testing lift equipment have been developed in the past. However, the performance reliability and ease of use of the conventional equipment have been unsatisfactory. There is a need for a higher performance testing device that is simple, safe and ergonomic to use.

SUMMARY OF INVENTION

The method of the present invention provides a solution to the above-outlined problems. The method is for testing load equipment. A trolley is provided that has first and second wheels, connected by an axle, in operative engagement with a housing. The housing has an upwardly sloping front segment and an upwardly sloping rear segment. A first set of upwardly directed flat weights are stacked side-by-side on the front segment and a second set of upwardly directed flat weights are stacked side-by-side on the rear segment so that the weights lean towards each other. The trolley together with the first and second sets of weights has a center of gravity above the axle. A brake support, attached to the front segment, projects downwardly from the front segment. The trolley is balanced on the set of wheels. The trolley is rolled on a ground. The trolley is stopped by engaging the brake support against the ground so that the front segment is substantially parallel to the ground. Weights are added or removed from the trolley by downwardly inserting or upwardly pulling, respectively, the weights without removing any of the wheels. The trolley is connected to a lifting equipment. The lifting equipment lifts the trolley from the ground to test the lifting capacity of the lifting equipment.

BRIEF DESCRIPTION. OF DRAWINGS

FIG. 1 is a side view of the test load trolley of the present invention in a balanced position;

FIG. 2 is a side view of the test load trolley of the present invention in a forward leaning position;

FIG. 3 is a front view of the test load trolley of the present invention;

Figure 4C:
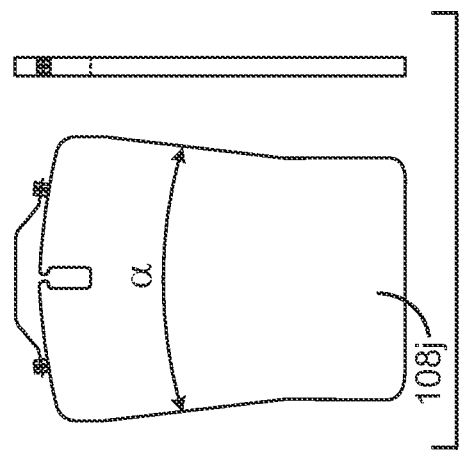
Figure 4B:
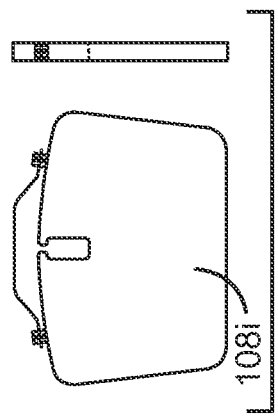
Figure 4A:
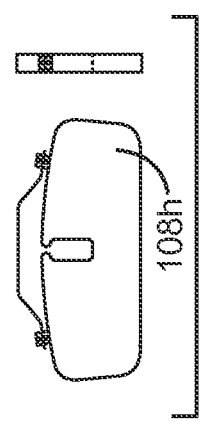
Figure 5:
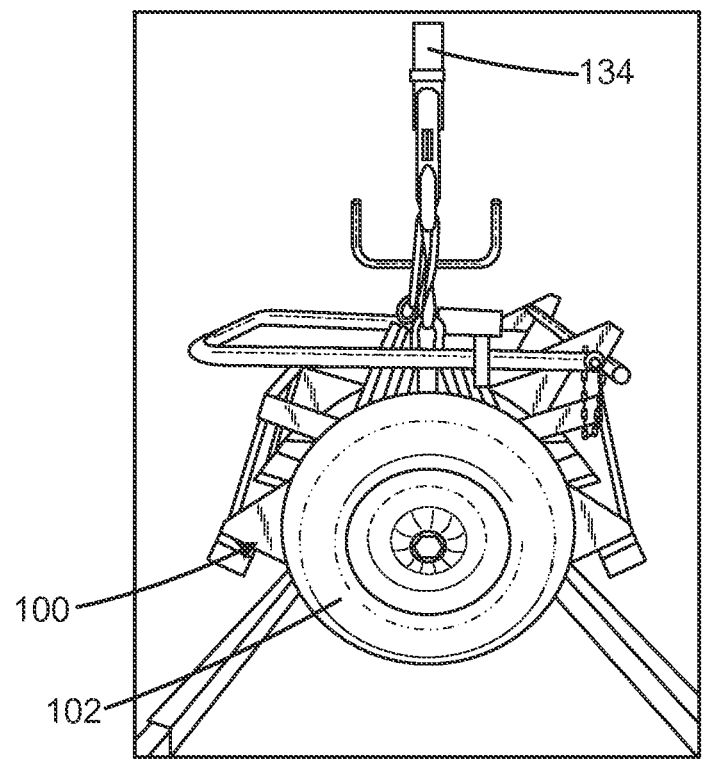

FIGS. 4a-c are front views of conical-shaped weights of the present invention; and FIG. 5 is a perspective side view of the test load trolley of the present invention being lifted by a lifting equipment to be tested.

DETAILED DESCRIPTION

With reference to FIGS. 1-3, the test load trolley 100 of the present invention has a pair of wheel 102, connected by an axle 104, in operative engagement with or mounted on a housing 106. The trolley may be manually driven or driven by a motor. An elongate telescopic and/or foldable shaft 105, having a handle 107, is removably connected to the housing 106. A first set of flat weights 108a-g are placed on a front section 110 of the housing 106 and a second set of flat weights 112a-q are placed on a rear section 114 of the housing 106. The weights may be tightened to each other and to the housing with suitable bands/belts/ropes. Preferably, the weights 108, 112 are stacked in an upright position and balanced around a mid-point 116. The weights 108 are leaned towards the weights 112 to balance the trolley 100 so that the common center of gravity 118 is disposed above the axle 104. The weights may be added to or removed from the trolley 100 with one hand without removing any of the wheels 102. The weights are simply pulled or slid upwardly from the trolley to remove the weights or slid downwardly to add weights to the trolley, as needed. One advantage of having the weights stacked in the upright position is that the center of gravity only changes marginally as more weights are added to the trolley. This is important because even if a large number of weights are placed on the trolley 100 the center of gravity does not change much so that the trolley is still relatively easy to handle. If the weights had been stacked vertically on top of one another, the center of gravity changes dramatically as more weights are added and the trolley would eventually become unstable and difficult to handle. The placement of horizontally directed weights on top of another would also require two hands to lift, particularly if the weights are very heavy. In contrast, the weights of the current invention may easily be pulled up by one hand.

The trolley 100 has one centrally positioned hanging loop 130 or many hanging loops 130 disposed along a side of the trolley 100 for hanging the trolley 100 in a hook 133 of a cord/rope connected 132 to the lifting equipment 134 to be tested. The trolley 100 also has pulling loops 136, 138 at the front and rear of the trolley for pulling the trolley up and down stairways and other sloping surfaces. Preferably, the trolley 100 should be balanced prior to pulling it with, for example, a winch since the trolley and the weights are so heavy.

The housing 106 has upwardly sloping front segment 109 and rear segment 111 so that an angle alpha is formed between the segments 109 and 111 and the ground/floor 120 when the trolley 100 is placed in a balanced position (see FIG. 1). In this way, the segments 109 and 111 form a V-shaped floor of the housing 106. The angle alpha may be about 20° but other angles may be used such as angles ranging from 1° to about 45° as needed.

The trolley 100 may have a rubber front support brake 140 and a rubber rear support brake 142 that provide support for the trolley 100 against the floor 120 and prevents it from undesirably sliding on the floor when the trolley 100 is stationary.

The weights may be flat but also conical so that the weights are wedged against one another and against the side wall of the housing and are not rested on the segments 109 and 111 are they are stacked against one another. Conical-shaped weights 108h-j are shown in FIGS. 4a-c, respectively. The weights on the rear segment 111 may be conical-shaped also in the same way as the flat weights 108h-j. The conical shape of the weights reduced the risk of the weights moving back and forth as the trolley is moved since the conical-shaped flat weights are placed/stacked against one other and each weight is wedged against the wall of the housing 106. In this way, there is no need to tighten the weights together with a fastener. When the weights are wedged against one another to form an arch shape they do not stand on the front segment 109 or the rear segment 111 but are held in place above the segments by vertical side walls on the housing without necessarily touching the segments 109, 111. Preferably, the length and the width of the trolley 100 should be kept to a minimum to make it easier to handle the trolley 100 in narrow and otherwise difficult environments.

An important feature of the trolley 100 is that the center of gravity 118 is right above the axle 104 to provide good balance and to make it easy to handle the trolley 100. In this way, the trolley 100 rests firmly on the ground/floor 120 when it is either leaned forwardly to rest on the front support 140 or leaned rearwardly to rest on a rear support 142. When the trolley 100 is leaned forwardly to rest on the support 140, the angle alpha increases to the angle beta, as best shown in FIG. 2. The angle beta may be about 40° if the angle alpha is 20°. As mentioned earlier, the weights 108, 112 of the trolley 100 also reduce the risk of the trolley 100 sliding when in the rested position. As indicated above, the support brakes 140 and 142 may be used as brakes to reduce the speed of the trolley 100 by permitting the friction between the support 140 or 142 and the ground 120 reduce the velocity of the relatively heavy trolley 100. The breaking force is significant since the weight of the trolley is significant. In this way, the support brakes may be activated by, for example, leaning the handle 107 and shaft. 105 in a forward or rearward direction. If the floor is sloping, such as up to 5 degrees, the support brakes such as support brake 142, is used to slow down the trolley 100. The trolley 100 may also be pulled upwardly. The trolley 100 has a pivotal support leg 143 that is rotatably connected at the outer end of the rear segment 111. When the trolley 100 is moved forwardly to be supported by the support brake 140, the support leg 143 may be pivotally moved down to rest on the ground 120, as best shown in FIG. 2. In this way, there is a lower load on the wheels 102 particularly if or when the trolley 100 is tied by cords to other things such as a vehicle.

Another feature of the trolley 100 is that the center of gravity 118 is only slightly raised as more weights 108, 112 are added to the housing 106. This is because the weights are not stacked on top of one another but stacked in an upright position in forwardly and rearwardly relative to the axle 104 and the mid-point 116. This means the trolley 100 maintains its ease of handling even when more weights are added. An important feature of the present invention is that the handling performance of the trolley is almost independent of the number of weights used. The combination of trolley, the upwardly directed flat weights and the upwardly sloping front/rear segment gives almost the same handling performance of the trolley almost independent of the number of weights used.

In operation, the lifting capacity of the lifting equipment 134 to be tested by the trolley 100 is first determined such as 250 kg. The user then adds weights to the trolley 100 so that the weights plus the weight of the trolley 100 weigh 250 kg since the trolley will be lifted by the lift equipment to be tested also. If the trolley 100 is in a service car, the trolley may be rolled down a ramp from the car. Since the trolley and the loaded weight have a total weight of 250 kg, the user may slow down the velocity of the trolley 100 down the ramp by applying one of the supports 140, 142 against the ramp so that the friction therebetween slows down the trolley 100. When the trolley is pushed along a horizontal floor it is usually most effective to simply pull the handle 107 forward until the brake support 140 rubs against the floor to stop the trolley 100. If the trolley is pulled on a sloping floor the handle 107 may be lowered until the brake support 142 rubs against the floor to stop the trolley. The trolley is in this way transported to the lifting equipment and placed below the lifting equipment 134. The hook 133 may be connected to lifting bands 135 connected to one of many of the loops 136, 138 on the trolley. Optionally, the handle 107 and the shaft 105 are folded to make the trolley 100 very compact prior to lifting it. The lifting equipment 134 then lifts the trolley 100 that is loaded with the right number of weights 108, 112 so that the total weight is 250 kg. FIG. 5 shows the trolley 100 in a compacted position hanging in the lifting equipment 134. A second lifting equipment may then be tested in the same way. If the lifting capacity of the second lifting equipment is less such as 200 kg, the user simply removes 50 kg of the upright weights from the trolley 100 by sliding them upright by using one hand. Preferably, the same amount of weights should be removed from both sides to maintain the correct balance of the trolley 100.

While the present invention has been described in accordance with preferred compositions and embodiments, it is to be understood that certain substitutions and alterations may be made thereto without departing from the spirit and scope of the following claims.

The invention claimed is:

1. A method for testing load equipment, comprising:
providing a trolley having first and second wheels, connected by an axle, in operative engagement with a housing, the housing having an upwardly sloping front segment and an upwardly sloping rear segment, a first set of upwardly directed weights stacked side-by-side on the front segment and a second set of upwardly directed weights stacked side-by-side on the rear segment so that the weights and weights lean towards each other, the trolley together with the first and second sets of weights having a center of gravity above the axle, a brake support attached to the front segment projecting downwardly from the front segment;
balancing the trolley on the set of wheels;
rolling the trolley on a ground;
stopping the trolley by engaging the brake support against the ground so that the front segment is substantially parallel to the ground;
adding or removing weights from the trolley by downwardly inserting or upwardly pulling, respectively, the weights without removing any of the wheels;
connecting the trolley to a lifting equipment; and
the lifting equipment lifting the troll from the ground.

2. The method according to claim 1 wherein the method further comprises using conical shaped weights that are wedged against one another and/or against the housing.

3. The method according to claim 1 wherein the method further comprises balancing the weights around a mid-point.

4. The method according to claim 1 wherein the method further comprises connecting a loop attached to the trolley to a hook on a cord connected to the lifting equipment.

5. The method according to claim 1 wherein the method further comprises using a rear support brake for slowing down the trolley when moving along a sloping floor by engaging the support brake against the floor.

6. The method according to claim 1 wherein the method further comprises folding the handle and the shaft towards the housing prior to lifting the trolling.

* * * * *